United States Patent [19]

Michalko

[11] 4,083,886
[45] Apr. 11, 1978

[54] TRANSALKYLATION OF ALKYLAROMATIC HYDROCARBONS

[75] Inventor: Edward Michalko, Chicago, Ill.

[73] Assignee: UOP Inc., Des Plaines, Ill.

[21] Appl. No.: 763,483

[22] Filed: Jan. 28, 1977

Related U.S. Application Data

[63] Continuation-in-part of Ser. No. 671,894, Mar. 29, 1976, abandoned.

[51] Int. Cl.² ............................................. C07C 3/62
[52] U.S. Cl. ................................................ 260/672 T
[58] Field of Search ...................................... 260/672 T

[56] References Cited

U.S. PATENT DOCUMENTS

| | | | |
|---|---|---|---|
| 3,377,400 | 4/1968 | Wise | 260/672 T |
| 3,410,921 | 11/1968 | Pollitzer | 260/672 T |
| 3,437,710 | 4/1969 | Pollitzer | 260/672 T |
| 3,463,744 | 8/1969 | Mitsche | 260/672 T |
| 3,677,973 | 7/1972 | Mitsche et al. | 260/672 T |

*Primary Examiner*—C. Davis
*Attorney, Agent, or Firm*—James R. Hoatson, Jr.; Robert W. Welch; William H. Page, II

[57] ABSTRACT

A process for the transalkylation of alkylaromatic hydrocarbons is disclosed. Transalkylation of alkylaromatic hydrocarbons, such as toluene, is effected at transalkylation conditions in contact with a catalytic composite characterized by a method of preparation whereby a zeolite of the mordenite crystal structure with a sodium content of less than about 5 wt. % as $Na_2O$ is subjected to an aqueous ammoniacal treatment at a pH of at least about 9.5 and calcined in intimate admixture with a refractory inorganic oxide to form a catalytic composite therewith.

14 Claims, No Drawings

TRANSALKYLATION OF ALKYLAROMATIC HYDROCARBONS

CROSS-REFERENCE TO RELATED APPLICATIONS

This application is a continuation-in-part of a copending application Ser. No. 671,894 filed Mar. 29, 1976, now abandoned.

Crystalline aluminosilicates, or zeolites, of which mordenite is one example, are well known in the art and have found extensive application as hydrocarbon conversion catalysts or as a component thereof. Such materials are of ordered crystalline structure often visualized as a three-dimensional network of fundamental structural units consisting of silicon-centered $SiO_4$ and aluminum-centered $AlO_4$ tetrahedra, the tetrahedra being interconnected by a mutual sharing of apical oxygen atoms and arranged to form cages or cavities in open communication through smaller intracrystalline channels or pore openings whose narrowest cross section has essentially a uniform diameter characteristic of each crystalline aluminosilicate variety. To effect a chemical balance, each $AlO_4$ tetrahedra has a cation associated therewith — usually a sodium or other exchangeable cation. The aforementioned cages or cavities are occupied by water molecules and by the last mentioned cations, both of which exhibit considerable freedom of movement permitting ion-exchange and reversable dehydration.

The crystalline aluminosilicates, or zeolites, employed in the manufacture of the catalytic composite of this invention, are of the mordenite crystal structure, highly siliceous in nature and generally characterized by a silica-alumina mole ratio of from about 6 to about 12 as found in nature. The mordenite crystal structure comprises four- and five-membered rings of the $SiO_4$ and $AlO_4$ tetrahedra so arranged that the crystal lattice comprises pores and channels running parallel along the crystal axis to give a tubular configuration. This structure is unique among the crystalline aluminosilicates since the channels or tubes do not intersect, and access to the cages or cavities is in only one direction. For this reason, the mordenite structure is frequently referred to as two-dimensional. This is in contrast to other well-known crystalline aluminosilicates, for example faujasite, in which the cavities can be entered from three directions. Mordenite, clinoptilolite, or mordenite which has been synthesized or acid extracted, caustic extracted, or otherwise treated to increase the silica-alumina mole ratio to about 20:1 or more while maintaining the mordenite crystal structure, may be used in the manufacture of the catalytic composite of this invention.

Crystalline aluminosilicates having a mordenite crystal structure have heretofore been utilized composited with a refractory inorganic oxide, typically alumina, as a hydrocarbon conversion catalyst, and are particularly useful with respect to the transalkylation of alkylaromatic hydrocarbons. The transalkylation or disproportionation of alkylaromatic hydrocarbons is of particular importance in conjunction with catalytic reforming. In recent years, largely due to the success and growth of catalytic reforming and improved methods of separating and recovering aromatic hydrocarbons produced thereby, the petroleum industry has become a principal source of benzene, toluene, and other aromatic and alkylaromatic hydrocarbons. The supply and demand for specific aromatic hydrocarbons varies from time to time. For example, it is not uncommon to find toluene in excess of demand while benzene is in short supply. To obviate this situation, it is desirable to treat the toluene at transalkylation or disproportionation reaction conditions whereby one molecule is alkylated at the expense of another molecule which is dealkylated to yield benzene and xylenes or other polymethylated benzenes.

It is an object of this invention to present an improved process for the transalkylation of alkylaromatic hydrocarbons utilizing the novel composition as a catalyst therefor.

In one of its broad aspects, the present invention embodies a process for the transalkylation of alkylaromatic hydrocarbons which comprises treating an alkylaromatic hydrocarbon having from about 7 to about 15 carbon atoms per molecule in admixture with from about 1 to about 10 moles of hydrogen per mole of hydrocarbon at transalkyltion reaction conditions, including a temperature of from about 200° to about 480° C., in contact with a catalytic composite comprising a zeolite in intimate admixture with a refractory inorganic oxide in a weight ratio of from about 1:3 to about 3:1, said catalytic composite having been prepared by subjecting a zeolite of the mordenite crystal structure and containing less than about 5 wt. % sodium as $Na_2O$, to an aqueous ammoniacal treatment at a pH of at least about 9.5, and calcining the thus treated zeolite in intimate admixture with a refractory inorganic oxide to form a catalytic composite therewith.

One of the more specific embodiments relates to a process for the transalkylation of toluene which comprises treating said toluene in admixture with from about 1 to about 10 moles of hydrogen per mole of toluene at transalkylation conditions, including a temperature of from about 220° to about 460° C., in contact with a catalytic composite comprising mordenite in intimate admixture with alumina in a weight ratio of from about 1:3 to about 3:1, said catalytic composite having been prepared by subjecting mordenite, containing less than about 5 wt. % sodium as $Na_2O$, to an aqueous ammoniacal treatment with a pH of from about 10 to about 12 and at a temperature of from about 75° to about 200° C. in intimate admixture with alpha-alumina monohydrate, and calcining said zeolite in intimate admixture with said alumina to form a catalytic composite therewith.

Other objects and embodiments of this invention will become apparent in the following detailed specification.

In the manufacture of the catalytic composite of this invention, the zeolite is subjected to an aqueous ammoniacal treatment of a pH of at least about 9.5, and said treatment can be prior to admixture with the refractory inorganic oxide or after admixture therewith, the latter being preferred. The aqueous ammoniacal treatment can be effected at a temperature of from about 75° to about 200° C. over a period of from about 1 to about 24 hours. The treatment can be effected at substantially atmospheric pressure in an open vessel at about the reflux temperature of the aqeous ammoniacal solution albeit over a more extended period up to about 24 hours. The treatment is effective over a substantially shorter period, say from about 1 to about 10 hours at autogenous pressures utilizing a closed vessel. Suitable ammoniacal solutions include solutions of bases such as ammonium hydroxide, hydroxylamine, hydrazine, tetramethylammonium hydroxide, etc., or strong organic amines like methylamine, dimethyamine, ethylamine, diethylamine, propylamine, diisopropylamine, n-butylamine, t-butylamine, diisobutylamine, n-amylamine, n-hexylamine, ethylenediamine, hexamethylenediamine, benzylamine, aniline, piperazine, piperadine, and the like, the selected base being employed in sufficient concentration to provide a pH of at least about 9.5, and preferably from about 10 to about 12.

The crystalline aluminosilicate, or zeolite, employed herein as a starting material should contain, or should be treated to contain, less than about 5 wt. % sodium as $Na_2O$. The sodium can be reduced to an acceptable level by conventional and widely practiced ion-exchange techniques. Typically, ammonium cations are exchanged for sodium cations on treating the zeolite in contact with an aqueous ammonium salt solution, for example an aqueous ammonium chloride solution. The resulting ammonium-exchanged zeolite is thereafter heat-treated to effect thermal decomposition of the ammonium cations and formation of the hydrogen form of the zeolite. In any case, the treatment may be effected one or more times to reduce the sodium content to less than about 5 wt. % as $Na_2O$.

Refractory inorganic oxides for use in accordance with the method of this invention include the naturally occurring as well as the synthetically prepared refractory inorganic oxides. Suitable refractory inorganic oxides are such as alumina, silica, zirconia, titania, thoria, boria, magnesia, chromia, stannic oxide, and the like, as well as combinations and composites thereof, for example, alumina-silica, alumina-zirconia, alumina-titania, etc. Alumina is a preferred refractory inorganic oxide for use herein, particularly with respect to the manufacture of a catalytic composite for use in the transalkylation of alkylaromatic hydrocarbons. The alumina may be any of the various hydrous aluminum oxides or alumina gels such as alpha-alumina monohydrate of the boehmite structure, alpha-alumina trihydrate of the gibbsite structure, beta-alumina trihydrate of the bayerite structure, and the like, the first mentioned alpha-alumina monohydrate being preferred.

The zeolite may be combined in intimate admixture with the refractory inorganic oxide in any conventional or otherwise convenient manner. For example, the zeolite can be admixed with the alumina precursor subsequently converted to alumina to provide the zeolite in intimate admixture with the alumina. One preferred alumina precursor for use in this manner is a basic aluminum sulfate such as is precipitated from an aqueous solution of aluminum sulfate and ammonium hydroxide at a pH of about 6.

The zeolite may be combined in intimate admixture with the refractory inorganic oxide in any conventional or otherwise convenient manner to form spheres, pills, pellets, granules, extrudates, or other suitable particle shape. For example, the zeolite can be admixed with an acidic alumina sol such as results from digesting aluminum in hydrochloric acid under controlled conditions, and the mixture dispersed as droplets in a hot oil bath whereby gelation occurs with the formation of spheroidal gel particles. In this type of operation, it is essential that, prior to the ammoniacal treatment of this invention, the acid anion content of the gelation product be substantially completely neutralized and separated, for example, by aging the gelation product in an ammoniacal media and/or washing the gelation product with an aqueous ammoniacal solution in accordance with prior art practice. The method is described in greater detail in U.S. Pat. No. 2,620,314. A more preferred method comprises commingling the zeolite with a powdered refractory inorganic oxide, adding a binder and/or lubricant to the mixture, and compressing the mixture into pills or pellets of uniform size and shape. Alternatively, and still more preferably, the zeolite is mulled with a powdered form of the refractory inorganic oxide, and with a peptizing agent such as nitric acid, to form an extrudable dough. The dough can be pressured through a die of predetermined size to form extrudate particles utilized as such or rolled into spheres in a spinning drum prior to calcination. In any case, the zeolite can be subjected to the aqueous ammoniacal treatment herein contemplated either before being admixed with the refractory inorganic oxide or after being admixed therewith, the latter being preferred. The zeolite is preferably calcined in intimate admixture with the selected refractory inorganic oxide in a weight ratio of from about 1:3 to about 3:1.

Regardless of whether the zeolite is subjected to the aqueous ammoniacal treatment before or after admixture with refractory inorganic oxide, the treated zeolite is calcined in intimate admixture therewith to form a catalytic composite. Calcination is suitably in an air atmosphere at a temperature of from about 425° to about 750° C., preferably at a temperature of from about 475° to about 550° C., over a period of from about 0.5 to about 10 hours.

The present invention embodies a process which comprises treating an alkylaromatic hydrocarbon having from about 7 to about 15 carbon atoms per molecule at transalkylation conditions including a temperature of from about 200° to about 480° C. and a pressure of from about atmospheric to about 1500 pounds per square inch gauge (psig) in contact with a catalyst comprising essentially the catalytic composite of this invention to form products of higher and lower number of carbon atoms than said alkylarmomatic hydrocarbon. The preferred composition employed as the catalytic composite comprises mordenite in admixture with alumina, said mordenite comprising from about 25 to about 75 wt. % of said composite.

The alkylaromatic hydrocarbon feed stock can be a substantially pure alkylaromatic hydrocarbon of from about 7 to about 15 carbon atoms, a mixture of such alkylaromatic hydrocarbons, or a hydrocarbon fraction rich in said alkylaromatics. Suitable alkylaromatic hydrocarbons include alkylbenzenes and alkylnaphthalenes, preferably with an alkyl group of less than about 4 carbon atoms. The catalytic composite is particularly effective in the treatment of the more difficultly transalkylatable toluene to form benzene, xylenes, or other polymethylbenzenes.

The transalkylation, or disproportionation, reaction can be effected in contact with the catalytic composite of this invention in any conventional or otherwise convenient manner and may comprise a batch or continuous type of operation. A preferred type of operation is of the continuous type. For example, the above described catalyst is disposed in a fixed bed in a reaction zone of a vertical tubular reactor and the alkylaromatic feed stock charged in an upflow or downflow manner, the reaction zone being maintained at a temperature of from about 200° to about 480° C., preferably at a temperature of from about 220° to about 460° C. Although pressure does not appear to be an important variable with respect to the transalkylation reaction of this invention, the process is generally conducted in the presence of an imposed hydrogen pressure to provide from about 1 to about 10 moles of hydrogen per mole of hydrocarbon. However, there is no net consumption of hydrogen in the process, and the hydrogen charge is recovered from the reactor effluent and recycled.

The transalkylation reaction can be effected over a wide range of space velocities. In general, the process is conducted at a space veolocity of from about 0.2 to about 10. Space velocities herein referred to are liquid hourly space velocities, (LHSV) i.e., volume of charge per volume of catalyst per hour. While the catalytic composite prepared by the present method permits unusually high space velocities indicative of high activity, the catalytic composite is particularly noteworthy because of its relatively high stability at a high activity level.

The composite prepared in accordance with the method of this invention may be employed as a component of a catalyst comprising any of the several catalytically active metallic materials in the oxidized or reduced state. Of particular interest are those catalytic composites comprising one or more metals of Group VIB and VIII including molybdenum, tungsten, chromium, iron, nickel, cobalt, platinum, palladium, ruthenium, rhodium, osmium and iridium. Thus, the composite of this invention can be utilized advantageously as a catalyst or component thereof to effect a variety of hydrocarbon conversion reactions involving reaction conditions comprising a temperature in the 25°–760° C. range. The catalysts are particularly useful in effecting the hydrocracking of heavy oils, including vacuum residuals, to form petroleum products in the middle distillate range utilizing a temperature of from about 260° to about 1560° C. and pressures of from about 500 to about 1000 psig. Said hydrocarbon conversion reactions further include polymerization of olefins, particularly ethylene, propylene, 1-butene, 2-butene, isobutylene and also higher boiling olefins, at polymerization reaction conditions. The composite of this invention is also useful as a catalyst or component thereof in effecting the alkylation of isoparaffins with olefins or other alkylating agents including, for example, alkyl halides and the like; and also the alkylation of isobutane, isopentane, and/or isohexane with ethylene, propylene, 1-butene, etc., or mixtures thereof; and also the alkylation of aromatics with olefins or other alkylating agents, particularly the alkylation of benzene, toluene, etc., with propylene, butylene, and higher boiling olefins, including nonenes, decenes, undecenes, etc., the foregoing alkylation reactions being effected at alkylation conditions disclosed in the art. The composite of this invention is further useful in the isomerization of paraffins, particularly n-butane, n-pentane, n-hexane, n-heptane, n-octane, etc., or mixtures thereof, including isomerization of less highly branched chain saturated hydrocarbons to more highly branched chain saturated hydrocarbons such as the isomerization of 2- or 3-methyl pentane to 2,2- and 2,3-dimethylbutane, isomerization of napthenes, for example, the isomerization of dimethylcyclopentane to methylcyclohexane, isomerization of methylcyclopentane to cyclohexane, etc., at isomerization reaction conditions. Other hydrocarbon conversion reactions including the reforming of naphtha to gasoline, dehydrogenation of ethylbenzene to styrene, and hydrogenation of benzene to cyclohexane, are effectively catalyzed utilizing the composite of this invention as a catalyst or as a component thereof.

The following examples are presented in illustration of the process of this invention and are not intended as an undue limitation on the generally broad scope of the invention as set out in the appended claims.

EXAMPLE I

In this example, a catalytic composite of mordenite and alumina was prepared without the benefit of the aqueous ammoniacal treatment herein described. Thus, 595 grams of a commercial mordenite (H Zeolon) containing about 0.16 wt. % sodium as $Na_2O$ and 16 wt. % volatile matter, as evidenced by weight loss on ignition at 900° C., was thoroughly dry-mixed with 694 grams of a commercial alpha-alumina monohydrate (Kaiser medium) containing about 28% volatile matter. Approximately 20 milliliters of concentrated nitric acid and 420 milliliters of water was admixed therewith, and the mixture mulled to form an extrudable dough. The resulting dough was extruded through a 1/16 inch die and the extrudate segmented and balled in a spinning drum with the formation of 1/16–⅛ inch spheroidal particles. The spheroidal product was subsequently calcined in air at 500° C. for 1 hour.

EXAMPLE II

The preparation was repeated in accordance with the method of Example I except that the mordenite was subjected to an aqueous ammoniacal treatment and calcined in intimate admixture with the alumina, the aqueous ammoniacal treatment in this case being after admixture with the alumina pursuant to one preferred embodiment of this invention. In this instance, the spheroidal product of Example I was immersed in an aqueous solution of ammonium hydroxide containing 5 wt. % $NH_3$ and having a pH of about 11.6. Five volumes of the aqueous ammoniacal solution were employed per volume of spheroidal product treated. The treatment was at atmospheric pressure conditions utilizing a glass flask with an overhead condenser. The treatment was effected at reflux temperature — about 90° C., over a 16 hour period. The thus treated material was subsequently water-washed, dried, and calcined for 1 hour at 500° C.

EXAMPLE III

The preparation of Example I was again repeated except that the mordenite was subjected to an aqueous ammoniacal treatment and calcined in intimate admixture with the alumina, the aqueous ammoniacal treatment in this case being after admixture with the alumina and at an elevated pressure pursuant to one preferred embodiment of this invention. In this instance, the spheroidal product of Example I was sealed in a glass-linedrotating autoclave together with an aqueous ammoniacal solution substantially as described in Example II. The aqueous ammoniacal solution was employed in an amount equivalent to 2 volumes per volume of said spheroidal product. The autoclave was heated to 110° C. and the spheroidal product treated at this temperature under autogenous pressure conditions for 2 hours. The thus treated product was recovered, water-washed, dried and calcined at 500° C. for 1 hour. The above-described preparations were evaluated with respect to the transalkylation of toluene. In each case, toluene, in admixture with hydrogen to provide a hydrogen/hydrocarbon mole ratio of about 10, was charged downflow through a 50 cubic centimeter bed of approximately ⅛ inch spheroidal catalyst particles at a liquid hourly space velocity of 2.0, and at transalkylation conditions including a pressure of 500 psig. The temperature of the catalyst bed was adjusted to effect a 40% conversion of a toluene feed stock, the temperature in each case being taken as a measure of catalyst activity.

The catalytic composites of Examples I, II and III required temperatures of 475°, 381° and 368° C., respectively, the latter two being prepared according to the method of this invention.

EXAMPLE IV

The preparation of Example I was again repeated except that the mordenite therein described was subjected to an aqueous ammoniacal treatment prior to admixture with the alumina, the mordenite being subsequently calcined in intimate admixture with the alumina. In this example, the mordenite was first immersed in the aqueous ammoniacal solution of Example II. Five volumes of solution were employed per volume of mordenite. The aqueous ammoniacal treatment was effected under reflux conditions utilizing a glass flask equipped with an overhead condenser. The treatment was effected over a 16 hour period at substantially atmospheric pressure conditions, after which the mordenite was recovered and dried. The mordenite was thereafter thoroughly dry-mixed with the alpha-alumina monohydrate to provide a 50–50 weight mixture with 20 milliliters of concentrated nitric acid in 420 milliliters of water being subsequently added. After thorough mulling to provide an extrudable dough, the dough was extruded, segmented, and formed into spheres as heretofore described. The spheroidal product was calcined in air for 1 hour at 500° C. and thereafter evaluated with respect to the transalkylation of toluene in the described manner. A 40% conversion was achieved at 380° C.

EXAMPLE V

In this example, the mordenite employed was an ammonium ion-exchanged mordenite as opposed to the aqueous ammoniacal solution-treated mordenite of this invention. Thus, a solution of 260 grams of ammonium nitrate in 2340 cubic centimeters of water was used to ammonium ion-exchange 600 grams of the mordenite. The mordenite was slurried in 600 cc portions of the solution of about 55° C. for about ½ hour, the mordenite being recovered by filtration after each of three such ammonium ion-exchange treatments. After the final treatment the mordenite was dried at about 95° C. The mordenite was thereafter thoroughly dry-mixed with the alpha-alumina monohydrate to provide a 50–50 weight mixture with 20 milliliters of concentrated nitric acid in 420 milliliters of water being subsequently added. After thorough mulling to provide an extrudable dough, the dough was extruded, segmented and formed into spheres as heretofore described. The spheroidal product was calcined in air for 1 hour at 500° C., and thereafter evaluated with respect to the transalkylation of toluene in the described manner. A 40% conversion was achieved at 463° C.

EXAMPLE VI

A substantially pure mordenite (H Zeolon), in the form of extrudate particles was calcined in air for 1 hour at 500° C. and thereafter evaluated with respect to the transalkylation of toluene in the described manner. In this instance, a temperature of 508° C. was required to achieve a 40% conversion. In a separate experiment, the calcined extrudate was further treated with an aqueous ammoniacal solution substantially in accordance with the method of Example III, and then further calcined in air at 500° C. for 1 hour. Although the temperature required to effect a 40% conversion of toluene was reduced to 473° C., the temperature is substantially higher than that required when the treated mordenite is calcined in intimate admixture with alumina.

EXAMPLE VII

In the preparation of the catalyst pursuant to the present invention, the mordenite may be combined in intimate admixture with the alumina in any conventional or otherwise convenient manner. This example, together with Example VIII, demonstrates the effect of the method of catalyst preparation when the mordenite is intimately admixed with an acidic alumina sol subsequently converted to an alumina gel. In this example, an alumina chloride hydrosol, with an aluminum/chloride ratio of 1.22 and containing 13.5 wt. % aluminum, was prepared by digesting substantially pure aluminum pellets in hydrochloric acid in the presence of an excess of the aluminum reactant. To about 436 cc of sol (sp gr 1.35) was added 176.5 gm of H-Zeolon mordenite admixed with 400 cc of 28% aqueous hexamethylenetetramine (HMT) solution. The sol was maintained at about 5° C. during and subsequent to the mordenite-HMT addition thereto. The sol-mordenite-HMT mixture was thereafter dispersed as droplets in a hot (95° C.) oil bath and formed into spheroidal gel particles. The particles were aged in the hot oil bath for about 1.3 hours at 150° C. at a pressure of 100 psi. The aged spheres which achieved a pH of 8.7 during the pressure age, were subsequently washed for about 3 hours with dilute aqueous ammonia solution at 95° C., dried for 4 hours at 150° C. and finally calcined for 2 hours at 550° C. The spheroidal alumina-mordenite particles had an average bulk density of 0.58 gms.

Three catalysts were prepared in the described manner and each evaluated with respect to the transalkylation of toluene as heretofore described. The temperatures required to effect 40% conversion were 402°, 429° and 450° C. — a temperature spread of 48°.

While the catalyst of Example VII was subjected to an aqueous ammoniacal treatment as is commonly practiced to neutralize residual chloride for removal as ammonium chloride during the subsequent dilute aqueous ammonia wash, it will be apparent with respect to the following Example VIII that, in this instance, this is merely a necessary preliminary step to the aqueous ammoniacal treatment of this invention.

EXAMPLE VIII

Each of the catalysts of Example VII, having been evaluated in the described manner, were recovered and subjected to the aqueous ammoniacal treatment of this invention. Thus, each of the catalysts was sealed in a glass-lined rotating autoclave together with an aqueous ammoniacal solution containing 5 wt. % ammonia and having a pH of about 11.6. The aqueous ammoniacal solution was employed in an amount equivalent to 2 volumes per volume of spheroidal product. The autoclave was heated at 110° C. and the spheroidal product treated at this temperature under autogenous pressure conditions for 2 hours. The thus treated spheroidal particles were recovered, water-washed, dried and calcined at 500° C. for 1 hour.

Again, each of the catalysts was evaluated with respect to the transalkylation of toluene. The temperatures required to effect 40% conversion were respectively, 382°, 385° and 388° C., a spread of only 6°, and an average temperature of 385° C., 42° below the 427° average temperature of the previous Example VII.

I claim as my invention:

1. A process for the transalkylation of alkylaromatic hydrocarbons which comprises treating an alkylaromatic hydrocarbon having from about 7 to about 15 carbon atoms per molecule in admixture with from about 1 to about 10 moles of hydrogen per mole of hydrocarbon at transalkylation reaction conditions, including a temperature of from about 200° to about 480° C., in contact with a catalytic composite comprising a zeolite in intimate admixture with a refractory inorganic oxide in a weight ratio of from about 1:3 to about 3:1, said catalytic composite having been prepared by subjecting a zeolite in the mordenite crystal structure, and containing less than about 5 wt. % sodium as $Na_2O$, to an aqueous ammoniacal treatment at a pH of at least about 9.5, and calcining the thus treated zeolite in intimate admixture with a substantially acid anion-free refractory inorganic oxide to form a catalytic composite therewith.

2. The process of claim 1 further characterized in that the alkyl substituent of said alkylaromatic hydrocarbon comprises less than 4 carbon atoms.

3. The process of claim 1 further characterized in that said alkylaromatic hydrocarbon is an alkylbenzene.

4. The process of claim 1 further characterized in that said alkylaromatic hydrocarbon is toluene.

5. The process of claim 1 further characterized in that said transalkylation conditions include a temperature of from about 220° to about 460° C.

6. The process of claim 1 further characterized in that said zeolite is mordenite.

7. The process of claim 1 further characterized in that said refractory inorganic oxide is alumina.

8. The process of claim 1 further characterized in that said refractory inorganic oxide is an alpha-alumina monohydrate.

9. The process of claim 1 further characterized in that said zeolite is calcined in intimate admixture with said refractory inorganic oxide at a temperature of from about 425° to about 750° C.

10. The process of claim 1 further characterized in that said zeolite is calcined in intimate admixture with said refractory inorganic oxide at a temperature of from about 475° to about 550° C.

11. The process of claim 1 further characterized in that said aqueous ammoniacal treatment is effected at a pH of from about 10 to about 12.

12. The process of claim 1 further characterized in that said aqueous ammoniacal treatment is effected at a temperature of from about 75° to about 200° C.

13. The process of claim 1 further characterized in that said zeolite is subjected to said aqueous ammoniacal treatment in intimate admixture with said refractory inorganic oxide.

14. A process for the transalkylation of alkylaromatic hydrocarbons which comprises treating an alkylaromatic hydrocarbon having from about 7 to about 15 carbon atoms per molecule in admixture with from about 1 to about 10 moles of hydrogen per mole of hydrocarbon at transalkylation reaction conditions, including a temperature of from about 200° to about 480° C., in contact with a catalytic composite comprising a zeolite in intimate admixture with a substantially acid anion-free refractory inorganic oxide in a weight ratio of from about 1:3 to about 3:1, said catalytic composite having been prepared by gelling a mixture of an acidic alumina sol and a zeolite in the mordenite crystal structure, and containing less than about 5 wt. % sodium as $Na_2O$, washing the resultant zeolite-alumina gel mixture with an aqueous ammonia solution and drying and calcining, subjecting the calcined mixture to an aqueous ammoniacal treatment at a pH of at least about 9.5, and drying and calcining the thus treated zeolite-alumina gel mixture.

* * * * *